United States Patent
Banavara et al.

(10) Patent No.: US 9,907,323 B2
(45) Date of Patent: Mar. 6, 2018

(54) INFANT FORMULA TABLETS

(71) Applicant: Mead Johnson Nutrition Company, Glenview, IL (US)

(72) Inventors: Dattatreya Banavara, Newburgh, IN (US); Juan M. Gonzalez, Newburgh, IN (US)

(73) Assignee: Mead Johnson Nutrition Co., Chicago, IL (US)

( * ) Notice: Subject to any disclaimer, the term of this patent is extended or adjusted under 35 U.S.C. 154(b) by 201 days.

(21) Appl. No.: 14/864,955

(22) Filed: Sep. 25, 2015

(65) Prior Publication Data
US 2017/0094991 A1  Apr. 6, 2017

(51) Int. Cl.
A23L 1/00 (2006.01)
A23L 1/29 (2006.01)
A23L 1/305 (2006.01)
A23L 1/30 (2006.01)
A23L 1/308 (2006.01)

(52) U.S. Cl.
CPC .......... *A23L 1/0026* (2013.01); *A23L 1/296* (2013.01); *A23L 1/30* (2013.01); *A23L 1/305* (2013.01); *A23L 1/3006* (2013.01); *A23L 1/3008* (2013.01); *A23L 1/3014* (2013.01); *A23L 1/3082* (2013.01); *A23V 2002/00* (2013.01)

(58) Field of Classification Search
CPC ........ A23L 1/0026; A23L 1/296; A23L 1/305; A23L 1/3006; A23L 1/3008; A23L 1/30; A23L 1/3014; A23L 1/3082
USPC .......................................................... 426/61
See application file for complete search history.

(56) References Cited

U.S. PATENT DOCUMENTS

| | | |
|---|---|---|
| 3,241,975 A | 3/1966 | Brochner |
| 5,374,657 A | 12/1994 | Kyle |
| 5,397,591 A | 3/1995 | Kyle et al. |
| 5,550,156 A | 8/1996 | Kyle |
| 5,849,324 A | 12/1998 | Dohnalek et al. |
| 5,902,578 A | 5/1999 | Halpin-Dohnalek et al. |
| 6,048,557 A | 4/2000 | van den Burg et al. |
| 6,667,068 B2 | 12/2003 | Smith |
| 6,953,592 B2 | 10/2005 | Darbyshire et al. |
| 7,070,804 B2 | 7/2006 | Gianesello et al. |
| 7,070,825 B2 | 7/2006 | Ndife et al. |
| 7,182,959 B2 | 2/2007 | Martani |
| 7,575,760 B2 | 8/2009 | Gianesello et al. |
| 7,635,675 B2 | 12/2009 | Opawale et al. |
| 7,867,545 B2 | 1/2011 | Friedman |
| 8,101,226 B2 | 1/2012 | Erdmann et al. |
| 8,828,471 B2 | 9/2014 | Shibata et al. |
| 8,974,847 B2 | 3/2015 | Toyoda et al. |
| 2007/0269515 A1 | 11/2007 | Henriksen et al. |
| 2008/0187583 A1 | 8/2008 | Massing et al. |
| 2009/0130243 A1 | 5/2009 | Inoue et al. |
| 2009/0175998 A1 | 7/2009 | Shibata |
| 2011/0236555 A1 | 9/2011 | Toyoda et al. |
| 2011/0244107 A1 | 10/2011 | Toyoda et al. |
| 2013/0078357 A1 | 3/2013 | Shibata et al. |
| 2013/0266693 A1 | 10/2013 | Leuenberger et al. |
| 2014/0099388 A1 | 4/2014 | Wang et al. |
| 2014/0170265 A1 | 6/2014 | Castillo |
| 2014/0255537 A1 | 9/2014 | Banavara et al. |
| 2014/0287089 A1 | 9/2014 | Hoijer et al. |
| 2014/0377440 A1 | 12/2014 | Shibata et al. |

FOREIGN PATENT DOCUMENTS

| | | | |
|---|---|---|---|
| EP | 1048216 | 11/2000 | |
| WO | WO2004023896 | * 3/2004 | ............... A23L 1/29 426/41 |

* cited by examiner

*Primary Examiner* — Hamid R Badr
(74) *Attorney, Agent, or Firm* — OspreyIP, pllc; James R. Cartiglia

(57) ABSTRACT

A nutritional compositions in a compressed solid form comprising about 5 to about 35% by weight of protein, about 5 to about 50% by weight percent of fat, and about 40 to about 70% by weight percent of carbohydrate, wherein the compressed solid form is readily dissolvable in water and has a moisture level of 4 to 17%. The nutritional composition, in certain embodiments, eliminates the need for scooping powder into narrow bottles, eliminates the need for transportation of loose powders for later reconstitution, and provides more precise serving sizes to ensure proper delivery of nutrients per feeding, while remaining readily dissolvable upon contact with a liquid. The disclosure further provides process for preparing a nutritional composition in a compressed solid form comprising cooling a powdered nutritional composition, contacting the cooled powdered nutritional composition with moisture, compressing the powdered nutritional composition under pressure, and drying the nutritional composition.

15 Claims, No Drawings

INFANT FORMULA TABLETS

TECHNICAL FIELD

The present disclosure relates to nutritional compositions in compressed solid form, useful as infant and children's formulas. The compressed solid nutritional compositions provide a convenient form compared to powdered or liquid compositions. Additionally, the disclosure relates to improved processes for preparing nutritional compositions in a compressed solid form.

BACKGROUND

Nutritional compositions, such as infant formula and growing-up milks, are typically provided as loose powders, liquids, or liquid concentrates. While these forms are generally ready to mix, or in the case of liquid compositions, require no mixing, they each have disadvantages. Powdered compositions can spill, be messy to measure, and may be difficult to dispense into a vessel with a narrow opening, as is typical for many infant nursing bottles. Liquid compositions are not as convenient to transport and generally lack the same shelf life as powdered formulations. Once a sealed container of liquid formula is opened, it must be used within a short period of time or refrigerated. Moreover, oxidation of components of the composition can occur after opening, resulting in a reduced shelf-life. Additionally, liquid formulations can be subject to spilling easily during transport, and may pose difficulties during airline travel due to restrictions on permissible liquid volumes.

Still, the classical approach of using pressure and adjuvants to create compressed forms from powders is not reliable for the production of nutritional formula tablets. Nutritional formulas like infant formula powders contain fats that due to their flow properties may be squeezed out during compression, may locate at the tablet surface and limit the tablet dissolution properties. If dissolution rates are slow, this can render the compressed solid form less practical.

Accordingly, there is a need for nutritional compositions in a compressed solid form, and processes for making the same, where the mobility of the fat is controlled and restricted, and the compressed form is readily dissolvable in water.

BRIEF SUMMARY

The present disclosure provides a nutritional composition in a compressed solid form, such as a tablet. In certain embodiments, the nutritional composition comprises about 21 to about 35% by weight of protein, about 5 to about 50% by weight of fat, and about 40 to about 60% by weight of carbohydrate. In particular embodiments, the compressed solid form is readily dissolvable in water.

In certain embodiments, the composition further comprises a source of long chain polyunsaturated fatty acids, a prebiotic composition comprising polydextrose and galactooligosaccharide, nucleotides, vitamins and minerals. In further embodiments, the nutritional composition comprises a probiotic.

The present disclosure further includes processes for preparing compressed solid nutritional compositions. In certain embodiments, the compositions can be prepared by cooling a powdered nutritional composition to a temperature below 11° C., contacting the cooled powdered nutritional composition with moisture, compressing the powdered nutritional composition under a pressure of 1-100 pounds per square inch (psi) (0.07-6.89 bars), and drying the compressed powdered nutritional composition.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

"Nutritional composition" means a substance or formulation that satisfies at least a portion of a subject's nutrient requirements. The terms "nutritional(s)", "nutritional formula(s)", "enteral nutritional(s)", "nutritional composition(s)", and "nutritional supplement(s)" are used interchangeably throughout the present disclosure to refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults, such as women who are lactating or pregnant.

The term "enteral" means through or within the gastrointestinal, or digestive, tract. "Enteral administration" includes oral feeding, intragastric feeding, transpyloric administration, or any other administration into the digestive tract.

"Pediatric subject" means a human that is less than 13 years of age. In some embodiments, a pediatric subject refers to a human subject that is less than 8 years old. In other embodiments, a pediatric subject refers to a human subject between 1 and 6 years of age. In still further embodiments, a pediatric subject refers to a human subject between 6 and 12 years of age.

"Infant" means a subject having an age of not more than about one year and includes infants from 0 to about 12 months. The term infant includes full term infants, pre-term infants, low birth weight infants (infants weighing less 2500 g at birth), very low birth weight infants (infants weighing less than 1500 g at birth), and extremely low-birth weight infants (infants weighting less than 1000 g at birth). "Pre-term" means an infant born before the end of the 37$^{th}$ week of gestation, while "full term" means an infant born after the end of the 37$^{th}$ week of gestation.

"Child" means a subject ranging in age from about 12 months to about 13 years. In some embodiments, a child is a subject between the ages of 1 and 12 years old. In other embodiments, the terms "children" or "child" refer to subjects that are between about one and about six years old, or between about seven and about 12 years old. In other embodiments, the terms "children" or "child" refer to any range of ages between about 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a term infant will, by definition, provide qualitatively and quantitatively adequate amounts of all carbohydrates, lipids, essential fatty acids, proteins, essential amino acids, conditionally essential amino acids, vitamins, minerals, and energy required for growth of the term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Nutritional supplement" or "supplement" refers to a formulation that contains a nutritionally relevant amount of at least one nutrient. For example, supplements described herein may provide at least one nutrient for a human subject, such as a lactating or pregnant female.

"Probiotic" means a microorganism with low or no pathogenicity that exerts a beneficial effect on the health of the host.

"Prebiotic" means a non-digestible food ingredient that beneficially affects the host by selectively stimulating the growth and/or activity of one or a limited number of beneficial gut bacteria in the digestive tract, selective reduction in gut pathogens, or favorable influence on gut short chain fatty acid profile that can improve the health of the host.

All percentages, parts and ratios as used herein are by weight of the total formulation, unless otherwise specified.

Compositions of the present disclosure may be free of substantially free of any optional or selected ingredients described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

As used herein, the term "about" should be construed to refer to both of the numbers specified in any range. Any reference to a range should be considered as providing support for any subset within that range.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

The present disclosure provides nutritional compositions in a compressed solid form, and processes for making them. The compressed solid forms are capable of improving the ease of use of nutritional compositions, such as infant formulas and growing-up milks. More particularly, the compressed solid forms provide for easy delivery and reconstitution when combined with water.

In an embodiment, the compressed solid nutritional composition comprises about 5 to about 35% by weight of protein, about 5 to about 50% by weight of a fat, and about 40 to about 70% by weight of a carbohydrate. In a particular embodiment, the compressed solid nutritional composition comprises about 21 to about 35% by weight of protein, about 20 to about 30% by weight of a fat, and about 40 to about 60% by weight of a carbohydrate. In a further embodiment, the compressed solid nutritional composition comprises about 10 to about 15% by weight of protein, about 20 to about 28% by weight of fat or lipid, and about 55 to about 60% by weight of carbohydrate. The compressed solid nutritional compositions are, in certain embodiments, prepared from powdered nutritional compositions. Powdered nutritional compositions include, without limitation, children's nutritional products, such as infant formula and growing-up milks, as well as adult nutritional compositions. In particular embodiments, the nutritional composition is an infant formula or a growing-up milk.

In certain embodiments, the powdered nutritional composition is suspended under gentle agitation or uniformly distributed onto a large surface area by means of, but not limited to, a vibrating conveyor belt or a vessel with agitation. The powdered nutritional composition is then cooled to a temperature below 11° C. Any suitable cooling device or refrigeration method may be used. Cooling the powdered nutritional composition quickly increases the solid fat content of the fat globules present in the powdered nutritional composition. Cooling temperature is determined by the solid fat content of the fat or lipid in powdered nutritional composition.

In some embodiments, the cooled powdered nutritional composition, which typically has a moisture content of less than 5%, is exposed to moisture by means of a fine particulate mist in order to bring the moisture content of the composition to a level of up to about 17%. In certain embodiments, the moisture content of the powdered nutritional composition is brought to between about 6% and about 17%; in other embodiments, the composition moisture level is brought to about 8% to about 10%. The mist can be created using, but not limited to, ultrasonic waves, fans, and spray nozzles. Particle size of the water mist can be in the range of 10-1500 nm, preferably 100-200 nm. In certain embodiments, the nano-mist is created using ultrasonic waves. The powder can be mixed or vibrated to achieve a uniform adhesion of moisture to the surface of the powder particles. This adhesion results in wetting the surface of the particles without dissolving or destroying the structure of the outer wall of the particles.

In still some embodiments, the temperature of the water mist is in the range of 1°-15° C., in order to reduce the flow properties of the fat or lipid used in the powder formulation. For instance, the pour (or flowing) temperature of some of the oils which can be used as a fat in the powdered nutritional composition, such as palm and coconut oils is 25°-35° C., while for sunflower, soybean and the algae-derived oils it is below 0° C. The use of cold water as the mist tends to reduce the mobility of the oils during the compression step and thereby reduces their presence on the surface of the tablets. The low temperature of the water mist also reduces the formation of fat-bridges that may lead to poor dispersibility of the tablet.

There is an inverse relationship between the rate of tablet dissolution and the presence of surface fat. Spray dried dairy powders, such as infant formula, have a higher proportion of the total fat covering the powder surface than entrapped inside the powder particulates. In some embodiments, 35-40% of the fat may be located on the powder surface.

In some embodiments, the surface of the powder particle contains carbohydrates in an amorphous form. These carbohydrates may be, but are not limited to, lactose, maltodextrins, and corn syrup solids. When the cold water mist comes into contact with the powder surface it hydrates some of these carbohydrates. These hydrated carbohydrates tend to form bridges, thereby increasing the stickiness of the powder particles.

In certain embodiments, the powdered nutritional composition may undergo solid carbon dioxide treatment prior to compression. The addition of this step would be based on the powdered nutritional composition characteristics and the desired porosity. It is possible to cool the powders by introducing fine particulates of solid carbon dioxide (10 um-1 mm), i.e. dry ice, during powder mixing. The dry ice sublimates and releases carbon dioxide gas that expands and removes air entrapped between the powder particles. The expelling of the air has the benefit of reducing the oxygen exposure of powder surface fat and minimizing detrimental lipid oxidation. The dry ice may also condense the available moisture in contact with the powders thus enabling the carbohydrate-to-carbohydrate bridge formation. It may also be possible to maintain the powder at a low temperature through the compression step by keeping some of the small dry ice particulates commingled with the powder. This would result in an increase in the internal porosity of the tablets upon sublimation of the dry ice.

In further embodiments, the moist powdered nutritional composition is transferred to a tableting unit for compression. The size and shape and weight of the tablet may vary depending on the serving size of the nutritional formulation and the number of tablets targeted to deliver that serving size. The tablets may have a smooth surface or have indentations that allow for penetration of the water to accelerate the rate of dissolution. The powder is placed in a tableting die and is quickly compressed at pressures of 1-100 psi; in certain embodiments, the powder is compressed in a tableting die and compressed at a pressure of 1-30 psi, and preferably at 5-10 psi. In some embodiments, compression is for a period of at least 3 seconds; in other embodiments, compression can be for about 3 seconds to about 20 seconds. In yet other embodiments, compression is for a period of about 3 seconds to about 10 seconds. A higher compression rate may compromise the tablet dissolution and may force the flow of the free fat to the surface of the tablet, thus compromising the wettability of the tablet. The use of a mild pressure range maintains some of the powder porosity. This porosity also allows for the diffusion of the carbon dioxide if dry ice is used during the process. The compression may take place at a controlled temperature range of 1-25° C., and preferably 2-8° C. The compressed tablet may then be transferred to the drying operation.

In some embodiments, the compressed tablets may be dried; in some embodiments the tablets are dried to a moisture level of between about 0.2% to about 5.0%. The drying operation may include, but is not limited to, use of a hot air tunnel, vacuum drying or freeze drying. During the process of drying, the particles adhere to each other and a process referred to as "particle stringing" occurs, depending on the glass transition and the molecular elasticity of the hydrating molecule. Vacuum drying allows the use of lower temperatures, such as 20°-60° C. to remove the moisture entrapped in the tablet. In embodiments where freeze drying is used during the drying operation, the temperature of the tablets is first reduced to between about 10° C. and 30° C. and the tablets are then subjected to mild heating to induce sublimation of the water to reach the target tablet moisture content. When solid carbon dioxide was used employed prior to compression, the sublimation would take place rapidly during the drying operation, thus providing additional porosity to the tablet and reducing the amount of air exposure to the formulation fats.

In some embodiments, the tablet dissolving properties of the compressed solid form may be enhanced by applying a coating to the tablet. This coating may use ingredients already available in the formulation or other materials approved for use in nutritional formulas especially the infant formula. These materials may be, but are not limited to, organic acid, fatty acids, phospholipids, salts, carbohydrates and proteins. Also, organic acids and bicarbonate salts may be combined in such a way that when hydrated would interact to create small microbubbles that would create additional action on the surface and inside the tablet to increase rate of dissolution without affecting the final pH of the reconstituted formula significantly. The coating can be applied by any means known in the art, and is, in certain embodiments, at a thickness of at least 1 mm; alternatively the coating is about 1 mm to about 5 mm in thickness.

The porosity of the compressed solid can be adjusted depending on the desired properties of the final product. For example, a higher porosity compressed solid composition is capable of dissolving more rapidly than a lower porosity compressed solid, but may not have sufficient hardness. In contrast, a lower porosity compressed solid is hard, with slower dissolution. In certain embodiments, it is preferred that the compressed solid formulation has sufficient hardness to avoid breakage during packaging and transport, while still maintaining a sufficiently rapid dissolution profile for the user's convenience. Accordingly, in certain embodiments, the compressed solid composition has a porosity of greater than about 60%, for example about 60% to 80%, or about 65 to about 70%. In alternative embodiments, the porosity is less than about 30%, for example about 10 to about 30%, or about 15 to about 25%.

The compressed solid form can be provided in any desired shape, such as a cube, tablet, sphere or disc, and can be any desired size. In one embodiment, the compressed solid form is about 5 to about 20 grams, or about 5 to about 15 grams. However, larger tablets may also be prepared. For example, in an embodiment the compressed solid form is provided as a single serving size of about 8 to 9 grams. An 8 to 9 gram sized compressed solid can conveniently be reconstituted in about 45 to about 55 mL of water, in order to provide a single liquid serving of the nutritional composition.

The compressed solid compositions provide a sufficient hardness to avoid breakage while being transported by the end-user. For example, it may be convenient, particularly in the case of infant formulas or growing up milks, to carry one or more compressed solid compositions in order to feed a pediatric subject while traveling. Unwanted breakage or crumbling of the solid may result in spilling of a portion of the serving. Accordingly, the compressed solids provided herein are, in certain embodiments, sufficiently hard to avoid breakage during travel, while being advantageously capable of dispersing or dissolving readily upon exposure to water. For example, a single serving size compressed solid is capable of dissolving in 22° C.-40° C. water within 30-80 seconds with the assistance of gentle shaking.

An exemplary embodiment of the process for preparing a compressed solid nutritional composition includes the following steps. A powdered nutritional composition, such as an infant formula or a growing-up milk, is uniformly distributed onto a large surface area by means of agitation. The powder is then cooled to a temperature below 11° C. using refrigeration. The powder is then place into contact with a nano-mist with particles in the size range of 100-200 nm via ultrasonic technology. The moist powder is then transferred to a tableting unit form compression, being compressed at pressures ranging from 5-8 psi. The compressed tablet is immediately transferred to the drying operation. The drying operation takes placed in a hot air tunnel and yields a final tablet with moisture content of 0.5-5%. Finally, the dried tablet may be coated with an organic acid or the like.

In some embodiments, the disclosure provides a fortified milk-based growing-up milk designed for children ages 1-3 years and/or 4-6 years, wherein the growing-up milk supports growth and development and life-long health. In some embodiments, the disclosure provides an infant formula suitable for infants ranging in age from 0 to 12 months, or from 0 to 3 months, 0 to 6 months or 6 to 12 months.

Suitable fat or lipid sources for the nutritional composition of the present disclosure may be any known or used in the art, including but not limited to, animal sources, e.g., milk fat, milk fat fractions and derivatives, tallow, lard, egg yolk lipids and derivatives; marine sources, such as fish oils and derivatives, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

Carbohydrate sources can be any used in the art, e.g., lactose, glucose, fructose, corn syrup solids, maltodextrins, sucrose, starch, rice syrup solids, and the like. The amount of carbohydrate in the nutritional composition typically can vary from between about 5 g and about 25 g/100 kcal.

The nutritional composition(s) of the disclosure may also comprise a protein source. In some embodiments, the nutritional composition comprises between about 1 g and about 7 g of a protein source per 100 kcal. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the proteins of the nutritional composition are provided as intact proteins. In other embodiments, the proteins are provided as a combination of both intact proteins and partially hydrolyzed proteins. For example, partially hydrolyzed proteins have, in some embodiments, a degree of hydrolysis between about 4% and about 10%. In certain other embodiments, the proteins are more completely hydrolyzed, such as to about 55%. In still other embodiments, the protein source comprises amino acids. In yet another embodiment, the protein source may be supplemented with glutamine-containing peptides. In particular embodiments, exogenous lysine is not included in the nutritional composition.

In a particular embodiment of the nutritional composition, the whey:casein ratio of the protein source is similar to that found in human breast milk. In an embodiment, the protein source comprises from about 40% to about 80% whey protein and from about 20% to about 60% casein.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (e.g., ATCC number 53103), *Bifidobacterium* species, *Bifidobacterium longum* (e.g. AH1205 or AH1206), and *Bifidobacterium animalis* subsp. *lactis* BB-12 (DSM No. 10140), *Bifi-*

*dobacterium infantis* (e.g. 35624), a spore-former such as *Bacillus coagulans* (e.g. ATCC PTA-6086, 6085, 6087, 11748), or any combination thereof.

If included in the composition, the amount of the probiotic may vary from about $1\times10^4$ to about $1\times10^{12}$ colony forming units (cfu) per gram of the nutritional composition. In another embodiment, the amount of the probiotic may vary from about $1\times10^6$ to about $1\times10^{12}$ cfu per gram of the nutritional composition. In still another embodiment, the amount of the probiotic may vary from about $1\times10^6$ to about $1\times10^9$ cfu per gram of the nutritional composition, or about $1\times10^9$ to about $1\times10^{12}$ cfu per gram of the nutritional composition. In yet another embodiment, the amount of the probiotic may be at least about $1\times10^6$ cfu per gram of the nutritional composition.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic, or developed through the genetic manipulation of organisms, whether such new source is now known or later developed.

The nutritional composition may also contain one or more prebiotics in certain embodiments. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain glucose, fructose, galactose, mannose, and xylose.

More specifically, prebiotics useful in the present disclosure may include polydextrose (PDX), polydextrose powder, lactulose, lactosucrose, raffinose, gluco-oligosaccharide, glucans, inulin, fructo-oligosaccharide, isomalto-oligosaccharide, soybean oligosaccharides, lactosucrose, xylo-oligosaccharide, chito-oligosaccharide, manno-oligosaccharide, arabino-oligosaccharide, siallyl-oligosaccharide, fuco-oligosaccharide, galacto-oligosaccharide (GOS), and gentio-oligosaccharides.

In an embodiment, the total amount of prebiotics present in the nutritional composition may be from about 1.0 g/L to about 10.0 g/L of the composition on a ready to feed basis. For example, in some embodiments, PDX may be included in the nutritional composition in an about of about 1.0 to 10.0 g/L In another embodiment, the amount of PDX is about 2.0 to about 8.0 g/L.

In certain embodiments, at least 20% of the prebiotics can comprise GOS, PDX or a mixture thereof. In an embodiment, the PDX and GOS have a PDX:GOS ratio of between about 9:1 and 1:9. In another embodiment, the ratio of PDX:GOS can be about 5:1 to 1:5. In yet another embodiment, the ratio of PDX*GOS can be between about 1:3 and 1:3. In further more particular embodiments, the ratio can be about 1:1 or 4:1. In another embodiment, the amount of the PDX*GOS combination may be between about 2.0 g/L and 8.0 g/L In a particular embodiment, the amount of the PDX*GOS combination may be about 2 g/L of PDX and 2 g/L of GOS. At least 20% of the prebiotics can comprise GOS, PDX, or a mixture thereof. The amount of each of GOS and/or PDX in the nutritional composition may, in an embodiment, be within the range of from about 1.0 g/L to about 4.0 g/L In other embodiments, the amount GOS and/or PDX is about 1 to about 10 g/100 kcal, about 2 to about 10 g/100 kcal, or about 4 to about 8 g/100 kcal of the powdered formulation.

The nutritional composition of the disclosure may contain a source of long chain polyunsaturated fatty acid (LCPUFA) that comprises docosahexaenoic acid. Other suitable LCPUFAs include, but are not limited to, α-linoleic acid, α-linoleic acid, linoleic acid, linolenic acid, eicosapentaenoic acid (EPA) and arachidonic acid (ARA).

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If included, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the subject. Alternatively, the DHA and ARA can be used in refined form.

In an embodiment, sources of DHA and ARA are single cell oils as taught in U.S. Pat. Nos. 5,374,657; 5,550,156; and 5,397,591, the disclosures of which are incorporated herein in their entirety by reference. Nevertheless, the present disclosure is not limited to only such oils.

The nutritional composition may also comprise a source of 1-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates. β-glucans may be differentiated in their origin by the presence of branching linkages. Cereal derived β-glucans have their linear portion formed by β-1,3 bonds and the branch segments by β-1-4 linkages. Yeast, mushroom and bacteria derived β-glucans have their linear portion formed by β-1,3 bonds and the branch segments by β-1-6 linkages. These branched structural differences can have significant implications in the biological activity of the β-glucan.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with (β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition(s) of the present disclosure may further comprise, in certain embodiments, nucleotides, including without limitation, cytidine 5'-monophosphate, uridine 5'monophosphate, adenosine 5'-monophosphate, guanosine 5'monophosphate, and mixtures thereof.

In an embodiment, the nutritional composition(s) of the present disclosure comprises choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes about 40 mg choline per serving to about 100 mg per 8 oz. serving.

In an embodiment, the nutritional composition comprises a source of iron. In an embodiment, the source of iron is ferric pyrophosphate, ferric orthophosphate, ferrous fumarate or a mixture thereof and the source of iron may be encapsulated in some embodiments.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In certain embodiments, the composition may optionally include one or more of the following vitamins or derivations thereof: vitamin $B_1$ (thiamin, thiamin pyrophosphate, thiamin triphosphate, thiamin hydrochloride, thiamin mononitrate), vitamin $B_2$ (riboflavin, flavin mononucleotide, flavin adenine dinucleotide, lactoflavin, ovoflavin), vitamin $B_3$ (niacin, nicotinic acid, nicotinamide, niacinamide, nicotinamide adenine dinucleotide, nicotinic acid mononucleotide, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In other embodiments, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolinate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound. However, in particular embodiments, the compositions do not include manganese gluconate, copper carbonate or zinc oxide.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

The amounts of vitamins and minerals in the children's nutritional composition may vary on a country by country basis. In an embodiment, the children's nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The children's nutritional composition of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 2 to about 7 g/100 kcal. The amount of protein typically can vary from about 1 to about 5 g/100 kcal. The amount of carbohydrate typically can vary from about 8 to about 14 g/100 kcal.

In some embodiments, the nutritional composition of the present disclosure is a growing-up milk. Growing-up milks are fortified milk-based beverages intended for children over 1 year of age (typically from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of an infant formula or a growing-up milk or other nutritional composition according to the present disclosure can vary from country to country, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels that depend on the nutrient contribution of regional cow's milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

EXAMPLE

Preparation of an Infant Formula Tablet

A powdered nutritional formulation with composition of about 11% protein, 27% fat, 57% carbohydrate, and a moisture content of 2% is suspended under gentle agitation in a fluidized bed and cooled to 8° C. The suspended powder is placed in contact with a water mist of 150 nm created by ultrasonic waves with a temperature between 8-10° C. The moist powdered composition is transferred to a tableting unit for compression. The tableting die is of cylindrical in shape and with 2.5 cm diameter. The tableting die is loaded with 8 gr of moist powder and it is compressed at pressures of about 8 psi at 5° C. for 5 seconds. The compressed tablet is then transferred to the drying belt oven with circulating air at 60° C. where it is dried to about 3% moisture Thus, the present disclosure provides a nutritional composition in a compressed solid form, and processes for making the same, which provides a practical nutritional solid form tablet which is readily dissolvable in water. In addition, the disclosed compressed solid form can also reduce the rate of oxidation of some of the components of the composition, such as the LCPUFAs, thus potentially providing a longer shelf life for the tablets.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicant reserves the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the versions contained therein.

What is claimed is:

1. A process for preparing a nutritional composition in a compressed solid form comprising:
   providing a powdered nutritional composition,
   cooling the powdered nutritional composition to a temperature below 11° C.,
   contacting the cooled powdered nutritional composition with moisture,
   compressing the powdered nutritional composition under a pressure of 1-100 psi, and
   drying the compressed powdered nutritional composition.

2. The process of claim 1, wherein the nutritional composition comprises:
   about 5 to about 35% by weight of protein,
   about 5 to about 50% by weight of fat, and
   about 40 to about 70% by weight of carbohydrate.

3. The process of claim 1, wherein the powdered nutritional composition is placed into contact with moisture by spraying it with a fine particulate mist.

4. The process of claim 3, wherein the fine particulate mist has a particle size of 10-1500 nm in size.

5. The process of claim 1, wherein contacting the powdered nutritional composition with moisture brings its moisture level to 4-17%.

6. The process of claim 5, wherein contacting the powdered nutritional composition with moisture brings its moisture level to 8-10%.

7. The process of claim 3, wherein the temperature of the fine particulate mist is 1° C.-15° C.

8. The process of claim 1, wherein the nutritional composition is an infant formula or a growing-up milk.

9. The process of claim 1, wherein compressing the powdered nutritional composition is under a pressure from about 5 to 8 psi.

10. The process of claim 1, wherein the compressed solid form is about 8 to about 9 grams.

11. The process of claim 9, wherein the compressed solid form dissolves in water having a temperature of 22°-40° C. within 30-80 seconds.

12. The process of claim 2, the nutritional composition further comprising about 5 to about 200 mg/100 kcal of a source of long chain polyunsaturated fatty acids.

13. The process of claim 12, wherein the source of long chain polyunsaturated fatty acids comprises docosahexaenoic acid and arachidonic acid in a ratio of about 1:3 to about 1:9.

14. The process of claim 2, wherein the nutritional composition comprises about 1 to about 10 g of a prebiotic composition per 100 kcal of nutritional composition, wherein the prebiotic composition comprises polydextrose and galacto-oligosaccharide.

15. The process of claim 2, the nutritional composition further comprising at least one probiotic.

* * * * *